US008565897B2

(12) United States Patent
Regnier et al.

(10) Patent No.: US 8,565,897 B2
(45) Date of Patent: Oct. 22, 2013

(54) AUTONOMOUS (LEADLESS) INTRACARDIAC IMPLANTABLE MEDICAL DEVICE WITH RELEASABLE BASE AND FASTENER ELEMENT

(75) Inventors: Willy Regnier, Longjumeau (FR); Martin Deterre, Paris (FR); Patrice Poussin, Rueil Malmaison (FR)

(73) Assignee: Sorin CRM S.A.S., Clamart Cedex (FR)

( * ) Notice: Subject to any disclaimer, the term of this patent is extended or adjusted under 35 U.S.C. 154(b) by 0 days.

(21) Appl. No.: 13/531,330

(22) Filed: Jun. 22, 2012

(65) Prior Publication Data

US 2012/0330392 A1 Dec. 27, 2012

(30) Foreign Application Priority Data

Jun. 24, 2011 (FR) ..................................... 11 55622

(51) Int. Cl.
*A61N 1/362* (2006.01)

(52) U.S. Cl.
USPC ......................................................... 607/119

(58) Field of Classification Search
USPC ......................................................... 607/119
See application file for complete search history.

(56) References Cited

U.S. PATENT DOCUMENTS 5,551,427 A 9/1996 Altman
6,141,588 A 10/2000 Cox et al.
6,354,299 B1 3/2002 Fischell et al.
7,580,751 B2 * 8/2009 Starkebaum .................... 607/40
2002/0165589 A1 11/2002 Imran et al.
2006/0136004 A1 6/2006 Cowan et al.
2007/0088397 A1 4/2007 Jacobson
2007/0293904 A1 * 12/2007 Gelbart et al. .................. 607/35

FOREIGN PATENT DOCUMENTS

WO WO 2007/047681 A2 4/2007

OTHER PUBLICATIONS

Foreign Search Report (Annexe Au Rapport De Recherche Preliminiare Relatif A La Demande De Brevet Francais No. FR 1155622 FA 752515), Jan. 16, 2012.

* cited by examiner

*Primary Examiner* — George Manuel
(74) *Attorney, Agent, or Firm* — Foley & Lardner LLP

(57) ABSTRACT

A leadless autonomous intracardiac implantable medical device having a releasable fastener system. This autonomous intracorporeal active medical device has two distinct elements connectable together and reversibly separable from one another, with a sealed capsule body (100) housing electronic circuitry (110), and a base (200) comprising a plate (202) having an outer face and an anchoring system on said outer face to anchor the base to a wall of an organ of a patient, and an inner face forming a support for the capsule body and having a fastening system to couple releasably the capsule body to the base. The capsule body comprises on its face turned towards the base at least one projection support (108) on an electrode surface for coming into contact with the wall of the organ of the patient when the capsule body is mounted on the base.

14 Claims, 4 Drawing Sheets

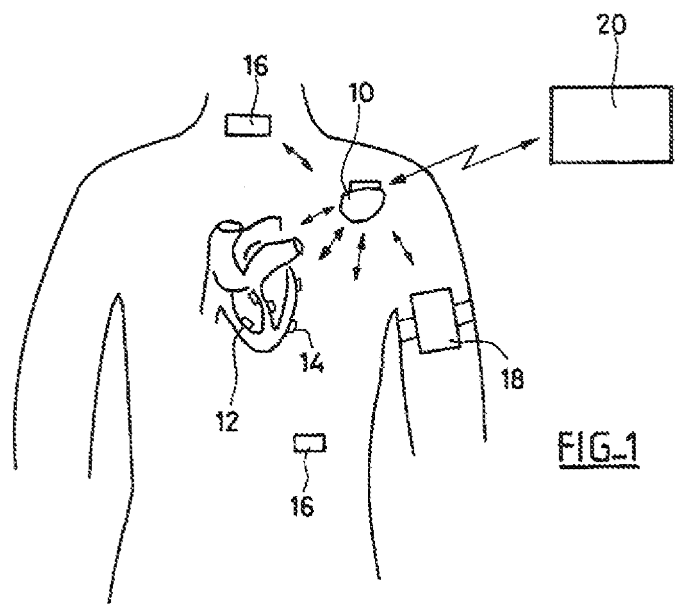
FIG_1
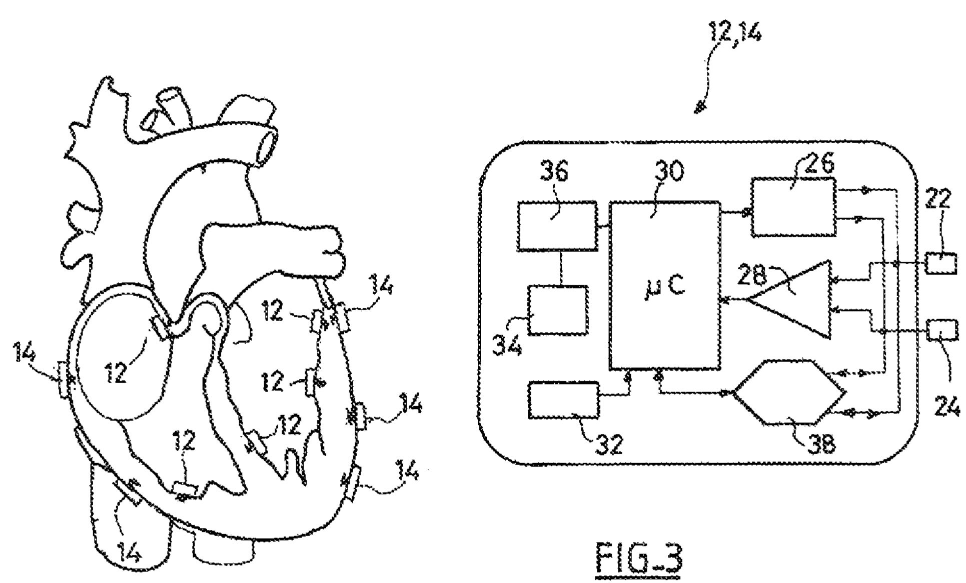
FIG_2
FIG_3

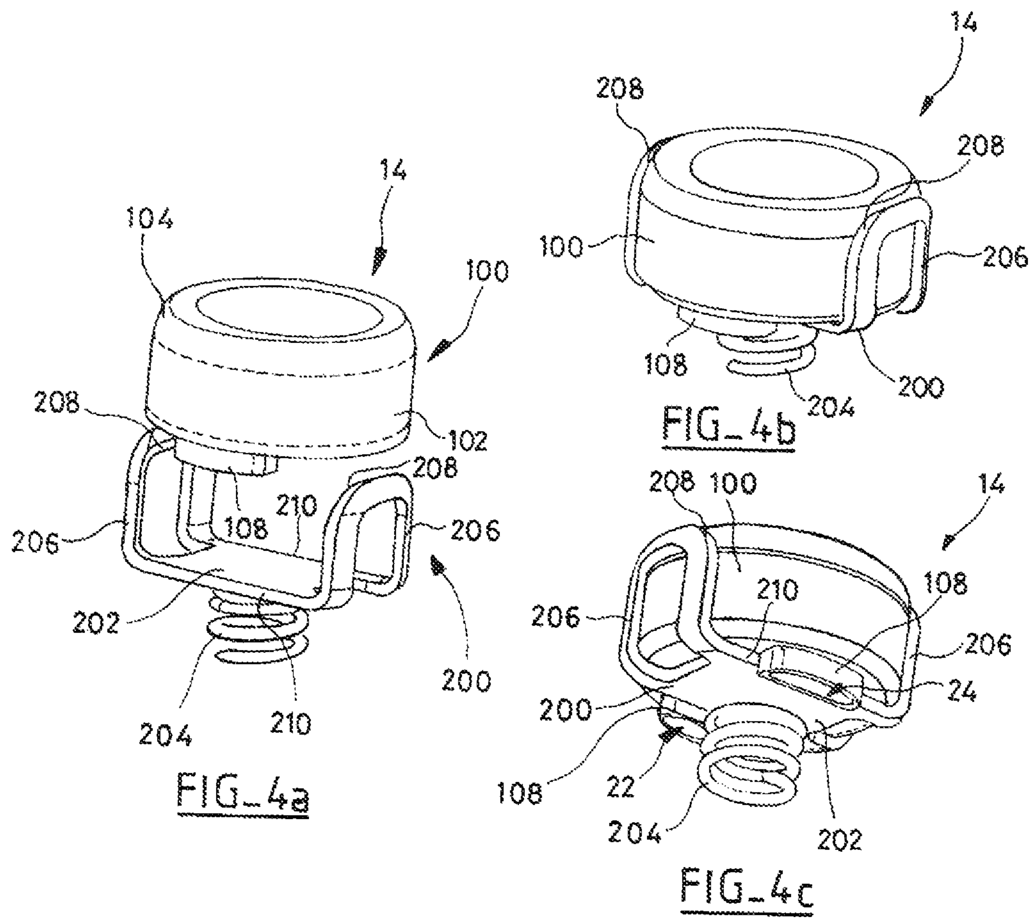
FIG_4a
FIG_4b
FIG_4c
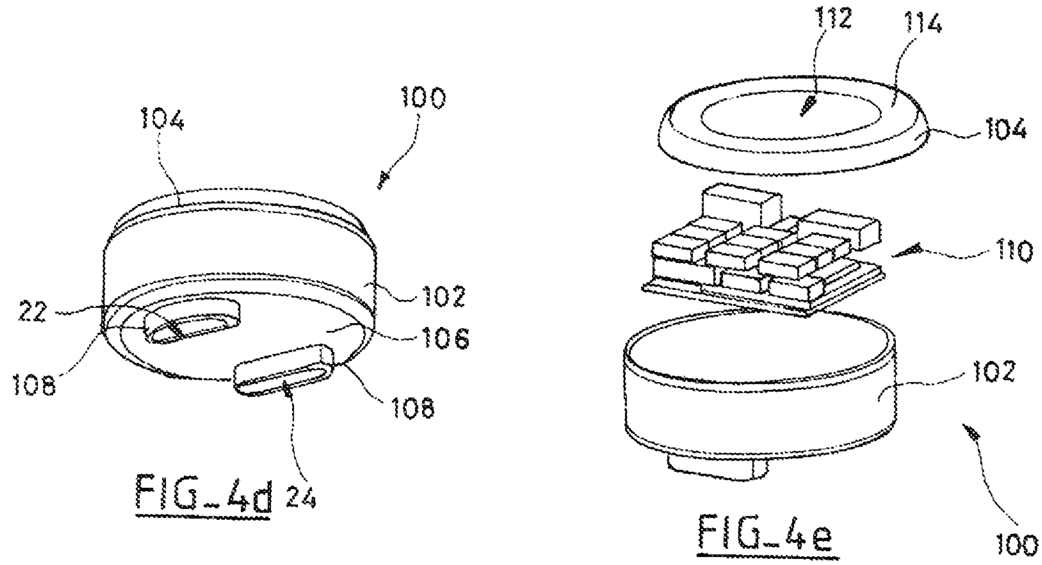
FIG_4d
FIG_4e

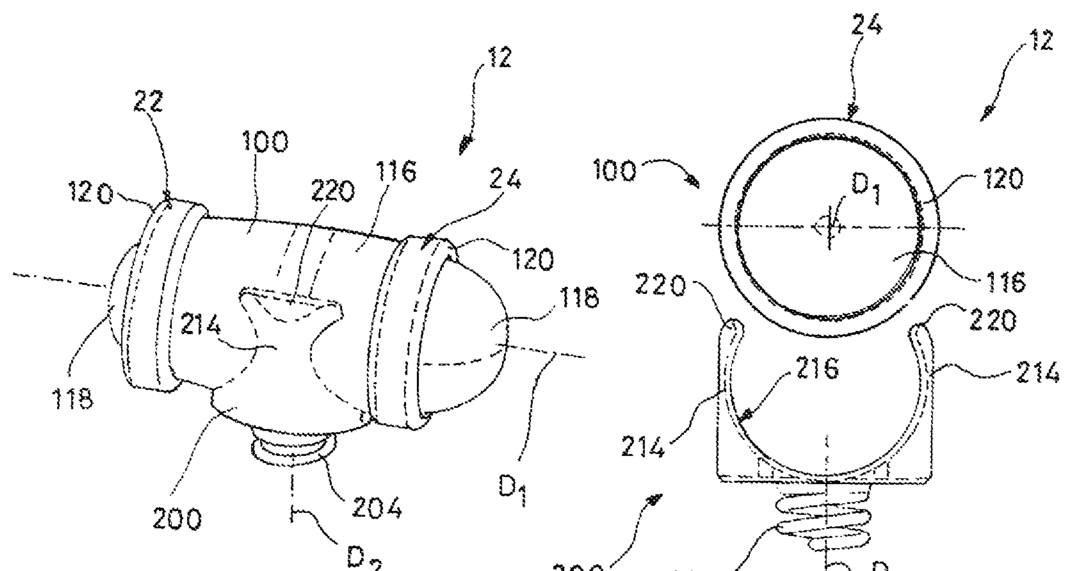
FIG_5a
FIG_5b
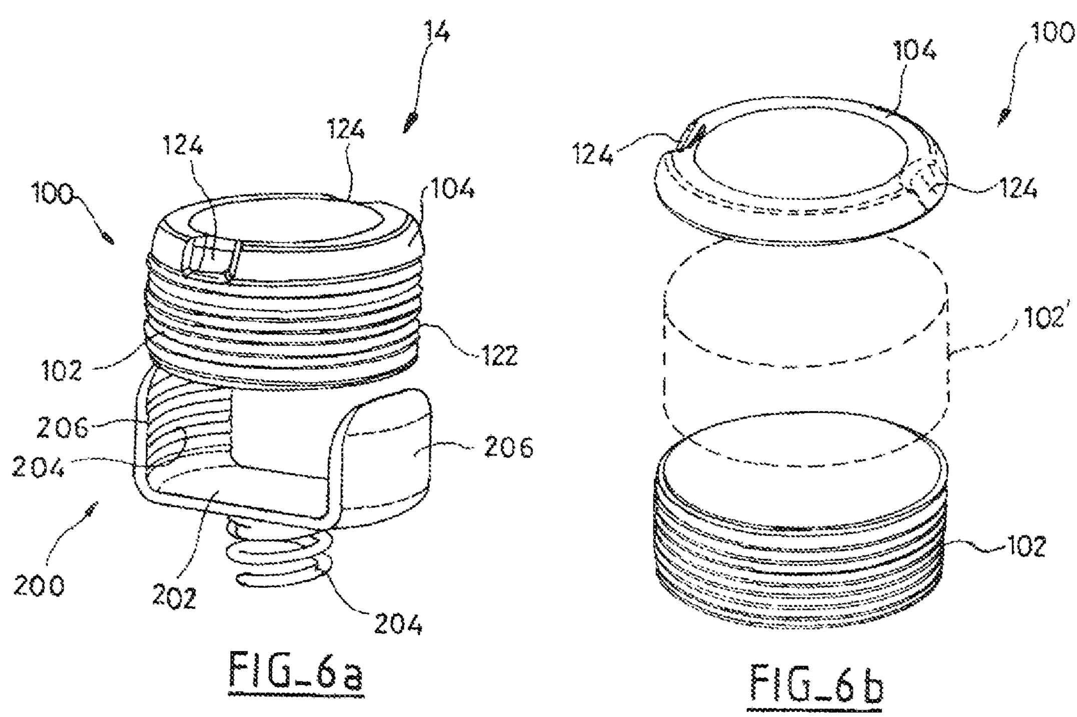
FIG_6a
FIG_6b

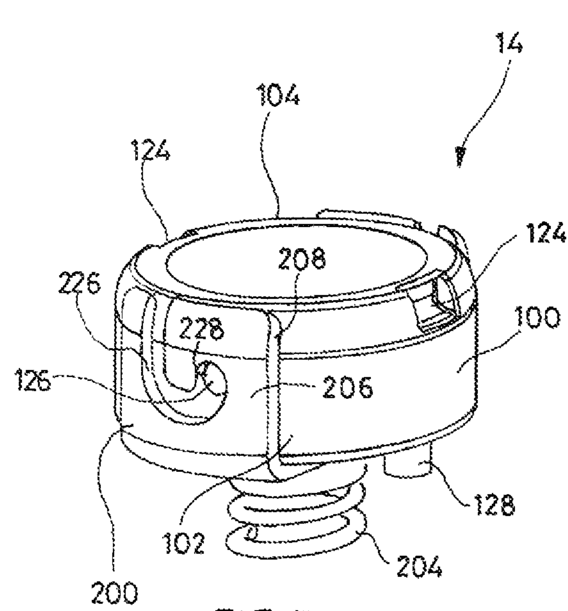
FIG_7a
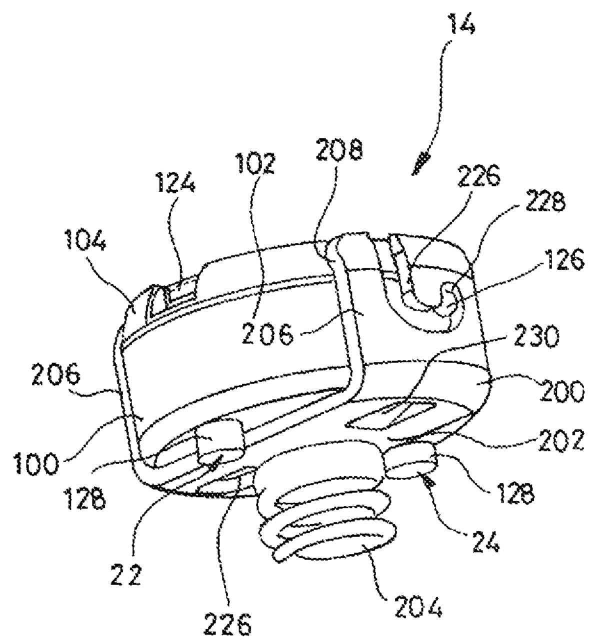
FIG_7b
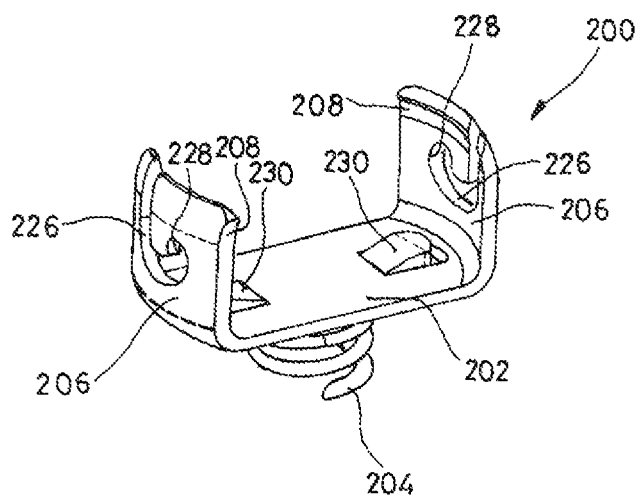
FIG_7c

AUTONOMOUS (LEADLESS) INTRACARDIAC IMPLANTABLE MEDICAL DEVICE WITH RELEASABLE BASE AND FASTENER ELEMENT

The present application claims the priority date benefit of French Patent Application No. 11/55622 entitled Leadless autonomous intracardiac implant with releasable fastener element" and filed Jun. 24, 2011, which is hereby incorporated by reference in its entirety.

FIELD

The present invention relates to "medical devices" as defined by the Jun. 14, 1993 Directive 93/42/EEC of the Council of the European Communities, more specifically to the "active implantable medical devices" as defined by the Jun. 20, 1990 Directive 90/385/EEC of the Council of the European Communities. This definition in particular includes devices that continuously monitor the cardiac rhythm and deliver if and as necessary to the heart electrical pulses for cardiac stimulation, resynchronization, cardioversion and/or defibrillation, in case of a rhythm disorder detected by the device. It also includes neurological devices and cochlear implants, as well as devices for pH measurement and for intracorporeal impedance measurement (such for measuring a transpulmonary impedance or an intracardiac impedance).

The present invention relates more particularly to those devices that involve autonomous implanted devices without any physical connection to a main (master) device that may be implanted (such as a generator for delivering stimulation pulses) or not implanted (such as an external programmer or device for remote monitoring of a patient). The autonomous implanted device communicates with the main or master device using a wireless communication technology.

BACKGROUND

Autonomous active implantable medical devices of the type involved in the present invention are also known as "leadless capsules" or more simply "capsules" to distinguish them from the electrodes or sensors placed at the distal end of a lead, which lead is connected at its opposite, proximal end, to a generator and is traversed throughout its length by one or more conductors connecting by galvanic conduction the electrode or the sensor to that generator. Such leadless capsules are, for example, described in U.S. Pat. Publication No. 2007/0088397 A1 and WO 2007/047681 A2 (Nanostim, Inc.) or in U.S. Pat. Publication No. 2006/0136004 A1 (EBR Systems, Inc.). These leadless capsules can be implanted epicardially, i.e., fixed to the outer wall of the heart, or endocardially, i.e., fixed to the inside wall of a ventricular or atrial cavity.

The attachment to the heart wall is usually obtained by a protruding anchoring helical screw, axially extending from the body of the capsule and designed to penetrate the heart tissue by screwing to the implantation site.

The leadless capsule typically includes detection/stimulation circuitry to detect (collect) depolarization potentials of the myocardium and/or to apply stimulation pulses to the implantation site (also called the stimulation site) where the capsule is located. The capsule then includes an appropriate electrode, which can be an active part of the anchoring screw, for electrically coupling to the mycocardium. It can also incorporate one or more sensors for locally measuring the value of a patient parameter, such as the oxygen level in the blood, the endocardial cardiac pressure, the acceleration of the heart wall, and the acceleration of the patient as an indicator of activity. Of course, for the remote exchange of data, the leadless capsules incorporate a transmitter/receiver for wireless communications with another device.

It should be understood however, that the present invention is not limited to one particular type of autonomous leadless capsule or implanted device, and is equally applicable to any type of leadless capsule, regardless of its functional purpose.

The energy source is one of the major weaknesses of leadless capsules because, being autonomous, it is not possible to provide energy through a lead conductor as with conventional or wired leads. Although energy harvesting devices and techniques have been proposed, to date only leadless capsules having battery power supply systems are truly operational. But given the very restrictive volume constraints, the autonomy of these batteries is limited, so that the currently available leadless capsules have a limited life span of around six months to two years, and must be regularly replaced.

The replacement of a leadless capsule, in addition to the frequent reiteration of a particularly invasive surgery, causes several problems:

- First, the former site of implantation, which was perhaps optimal (especially if it was determined according to a mapping optimization procedure) is not easily traceable;
- Second, further trauma to the tissues are caused by the explantation of the old device and the implantation of a new one; and
- Third, when the device at its end of life cannot be removed and must be left in place, it remains as a foreign and invasive parasitic element, which can become problematic over the years particularly with successive device implantations.

The above problems also arise elsewhere, regardless of the cause of the leadless capsule replacement, such as for a defective electronic circuit, replacement by a newer version device, and an element generating an infection.

Moreover, the introduction to the implantation site of a leadless capsule of a relatively large size requires tools of appropriate size, the use of which may be traumatic for the patient.

Finally, in all the systems proposed so far, the axis of fixation of the leadless capsule (typically, the axis of the anchoring screw) is the same as the axis of introduction of the device. For an endocardial device, this means that the anchoring system is at the end of the elongated cylindrical body constituting the body of the leadless capsule, which must necessarily be fixed perpendicularly to the heart wall. This configuration increases the invasiveness of the implanted system in relation to the heart function, particularly because of greater interference with blood flow and movement of the heart walls.

OBJECT AND SUMMARY

It is therefore an object of the present invention to provide a leadless capsule that, when it is to be replaced, permits:

- Reusing the same implantation site;
- Minimizing trauma to the tissues at the implantation site;
- Removing a capsule without leaving large sutures on the implantation site;
- Minimizing the invasiveness during implantation, and
- Increasing the design freedom for the shape of the capsule, particularly by avoiding to design an implantable elongated element, the largest dimension of which after implantation would be perpendicular to the heart wall.

In accordance with the present invention, an autonomous implantable device (leadless capsule) is of the type described in US Pat. Publication No. 2002/0165589 A1 cited above, in which the leadless capsule implanted is separated into two distinct components, with:

A first element or "base", dedicated to the attachment to the heart wall, comprising a conventional anchoring structure such as a screw, harpoon, hook or other penetrating element; and A second element or "capsule body" incorporating the main active components of the leadless capsule (e.g., the electronic circuits and the energy source(s)), wherein, the two elements are mechanically coupled together in a reversible manner (such that the coupled elements can be uncoupled) by a fastening system such as a clip, a screw, or a bayonet or other reversible mount.

During the system implantation, the first element (base) is attached first on the chosen stimulation site. Then, the second element (capsule body) is inserted and secured to the base through the fastening system.

In one embodiment, the fastening system comprises projecting tabs arranged so as to define opposing contact surfaces that are used to match to the shape of the corresponding contact surfaces of the capsule body. Preferably, there are two projecting tabs that are disposed at two opposite ends of the base.

As discussed in greater detail below, such a device according to the present invention can be adapted to both an elongated shape ("elongated shape" here meaning having a length that is greater than the diameter) endocardial leadless capsule, and flattened shape (a "flattened shape" here meaning having a diameter that is greater than the length) epicardial leadless capsule.

When intervention is necessary for the exchange of the capsule body (e.g., the battery is depleted, outdated system), the capsule body is simply detached from the base, and a new capsule body is installed in its place. Thus, the stimulation site is preserved and cardiac tissues do not suffer additional trauma due to extraction and/or re-implantation of the anchoring structure.

Moreover, such a concept significantly increases the modularity and adaptability of autonomous (leadless) implantable medical devices. Thus, for example, it is possible to define a family of capsule bodies that can be adapted to a standard base equipped with anchoring structure, without questioning the system implantation. Conversely, it is possible to consider a family of bases specifically designed for implantation in different parts of the heart, and likely to receive the same type of capsule body or a same family of capsule bodies.

Broadly, a device in accordance with one embodiment of the present of the invention is of the type described in US Pat. Publication No. 2002/0165589 A1 cited above and comprises two distinct elements connectable together and reversibly separable, with a sealed capsule body housing electronic circuits, and a base comprising a plate having an outer face with an anchoring structure that anchors the base to a wall of an organ of a patient, and a inner surface forming a support for the capsule body and having a fastening system to effect a mechanical coupling of the base to the capsule body. Preferably, mechanically coupling the base to the capsule body includes at least two projecting tabs arranged at two opposite ends of the plate, extending from the inner face of the base (away from the anchoring system), said tabs being substantially parallel and defining on their opposing faces contact surfaces matching the shape of the contact surfaces of the capsule body for making a mechanical coupling.

In one embodiment, the projecting tabs may be resiliently deformable, with the contact surfaces of the base having opposing concavities matching a corresponding pair of convex contact surfaces shape of the capsule body, so as to allow a reversible mechanical coupling (i.e., a fastening) of the capsule body to the base. The fastening system may use a friction fit coupling or a clip and locking detent fitment.

In one embodiment, the projecting tabs may be rigid with the contact surfaces of the base and comprising, for example, an internal thread engaging with a corresponding complementary threaded contact surface of the capsule body, so as to allow reversible screwing of the capsule body to the base. In an alternative embodiment, the projecting tabs are rigid and comprise a curved notch engaging with counterpart coupling fingers projecting from the capsule body, so as to allow for reversible nesting of the fingers in the notch in a bayonet mount style of fixing of the capsule body on the base. In the latter case, the base further comprises a resilient material positioned to bias the capsule body in the desired'axial direction so as to allow locking of the capsule body in position fixed to the base.

In one embodiment, the capsule body comprises a novel shaped surface feature whose major axis is oriented parallel to the axis of the anchoring structure, said body comprising, on its face turned towards the base, at least one projecting support with an electrode surface coming into contact with the tissues of the patient when the capsule is mounted on the base. A side wall of the projecting support can then be provided, for coming into contact with an edge of the plate so as to ensure axial blocking of any rotation of the capsule body relatively to the base. The anchoring structure axis is preferably oriented normal to the surface of the patient's tissue to which the base is anchored.

In one embodiment, the capsule body comprises electrodes coupled to contacts arranged on the inside of the base, these contacts being themselves connected to electrodes formed on the outer part of the base for coming into contact with the wall of the patient's organ to which the base anchoring system is affixed.

In one embodiment, the capsule body comprises, on its face opposite to that turned towards the base, a cover bearing a conductive surface forming a ground electrode, for coming into contact with a bodily fluid of the organ of the patient when the capsule body is mounted on the base.

One embodiment of the present invention concerns an implementation in which the capsule body comprises at least two elements that may be stacked or coupled together, preferably releasably coupled, such that a first capsule body has on its opposite face to that turned towards the base, a fastening system for fixing to a separable second capsule without separation of the first capsule body from the base. The fastening system used to form the stack of the two elements may be one of the types of fastening systems described herein for fastening the capsule body to the base. In this embodiment, the leadless capsule is formed by stacking of the first and second sealed capsule bodies and the base using such fastening systems. In a preferred embodiment, the first capsule, body contains the active components, and the second capsule body may include a power supply (e.g., a battery) for powering the electronic circuits housed in the first capsule body. In this embodiment, electrical contacts through the first and second capsule bodies are provided to electrically connect the power supply in the second capsule body to the electronic circuits in the first capsule body when the two are fastened together.

Another embodiment of the present invention concerns a capsule body with a novel shaped surface the axis of which is oriented perpendicularly to the axis of the anchoring system, and wherein the capsule body comprises, on at least one region of axial end, an annular ring with an electrode surface for coming into contact with the tissues of the patient when the capsule body is mounted on the base.

In all cases, the capsule body and/or the base can be advantageously provided with radiopaque markers to facilitate later extraction of the capsule body and then of setting up of a new capsule body fastened to the base, which remains implanted in situ.

DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements, and in which:

FIG. 1 schematically illustrates a set of medical devices, including leadless implantable medical devices, implanted within a patient's body;

FIG. 2 schematically illustrates more precisely how to implant these leadless implantable devices on the inner or outer myocardium wall;

FIG. 3 is a functional schematic block diagram showing the various stages constituting of a leadless capsule;

FIGS. 4*a* to 4*e* illustrate a first embodiment of a leadless capsule according to the present invention, for an epicardial capsule with clip fastening of the cap to the base;

FIGS. 5*a* and 5*b* illustrate a second embodiment of a leadless capsule according to the present invention, for an endocardial capsule with clip fastening of the capsule to the base;

FIGS. 6*a* and 6*b* illustrate a third embodiment of a leadless capsule according to the present invention, for a capsule body with epicardial fixation by screwing of the capsule body onto the base; and FIGS. 7*a* to 7*c* illustrate a fourth embodiment of a leadless capsule according to the present invention, for a capsule with epicardial fixation by a bayonet system fixing the capsule body to the base.

DETAILED DESCRIPTION

Various embodiments of the present invention will now be described with reference to the drawings FIGS. 1-7*c*. In FIG. 1 a set of medical devices implanted in the body of a patient is illustrated. The patient is implanted for example with a device 10 such as an implantable defibrillator/pacemaker/resynchronizer or a subcutaneous defibrillator or a long-term recorder. Device 10 is deemed the master device 10 of a network comprising a plurality of slave devices 12 to 18 with which it communicates intracorporally through human body communication ("HBC"). These devices may include intracardiac devices 12 or epicardial devices 14 (or both) directly implanted on the patient's heart, other devices 16 such as myopotential sensors or neurological stimulation devices, and possibly an external device 18 disposed, for example, an armband and provided with electrodes in contact with the patient's skin. Master device 10 can also be used as a gateway to the outside world to communicate with an external device 20, such as a programmer device or a device for remote transmission of data, with which they can communicate, for example, by RF telemetry.

Each of master and slave devices 10-18 is provided with at least one pair of electrodes that are in direct contact with body tissues for implanted devices, or in contact with the skin in the use of an external device 18.

With reference to FIG. 2, examples of leadless capsules implanted either on the inside part of the myocardium, in an atrial or ventricular cavity (endocardial implants 12) or on an outer wall of the same myocardium (epicardial implants 14) are shown. These devices are attached to the heart wall by means of a projecting anchoring screw for penetrating in cardiac tissue by screwing at the implant site. The screw can be a passive screw, only used for anchoring of the base, or an active screw, to collect the depolarization signals propagating in the tissues of the myocardium and/or to locally deliver stimulation pulses to the implantation site.

FIG. 3 schematically illustrates the internal electronic circuits of capsules 12 or 14. In this embodiment, each capsule includes a pair of electrodes 22, 24 connected to a stimulation pulse generator circuit 26 (for an active implantable medical device incorporating this function) and/or a detection circuit 28 for the collection of depolarization potentials collected between the electrodes 22 and 24. A central processor unit circuit 30 includes all of the circuitry to control the various functions of the implant, e.g., the storage of the collected signals. It comprises a microcontroller or microprocessor and an oscillator generating the clock signals needed for operating the microcontroller and communication. It may also contain an analog/digital converter and a digital storage memory. The capsule may also be provided with a sensor 32 such as an acceleration sensor, a pressure sensor, an hemodynamic sensor, a temperature sensor, an oxygen saturation sensor, etc.

The leadless capsule includes a power supply 34 which may be a small battery and/or an energy harvester circuit supplying all the electronic circuits via a power management stage 36. The electrodes 22 and 24 are also connected to a modulator/demodulator circuit 38 coupled to the central processor unit circuit 30 and emitting and/or receiving pulses used for wireless HBC communication. Thus, according to whether the stimulation circuit (module 26) and the detection circuit (module 28) are present or not, the electrodes 22, 24 can provide a single, double or triple function, namely: stimulation and/or detection of cardiac potentials (if applicable) and/or transmission of data monitored by the sensor 32 (if applicable) and emission/reception for the HBC communication (in any case).

Characteristically of the invention, and as illustrated in FIGS. 4-7, capsule 12 or 14 includes a capsule body 100 mounted on a base 200 by a reversible coupling fastening system.

FIGS. 4*a* to 4*e* illustrate a first embodiment of the present invention, for an epicardial capsule with clip fastening of capsule body 100 to base 200. In this embodiment, capsule body 100 comprises a flattened shape cylindrical body, typically of a few millimeters thick and from 8 to 12 mm in diameter, closed by a lid 104 at its upper part (that is to say on the side opposite to the wall on which the capsule body 100 is intended to be fixed to base 200).

The exterior of capsule body 100 can be made of titanium, according to a conventional stamping technology of a thin sheet of implantable titanium that complies with ISO 5832-2, or of any other biocompatible metal.

Alternatively, capsule 100 may be made of a biocompatible plastic material, by molding or any other technique to encapsulate the internal components housed capsule body 100. The biocompatible plastic can be for example, a Tecothane (registered trademark), which is a thermoplastic polyurethane based on a medical grade aromatic polyether and which may be radiopaque.

On its lower surface 106 (see especially FIG. 4*d*) capsule body 100 comprises two protrusions 108, including the surfaces intended to come into contact with heart tissue, which includes electrodes 22, 24 for sensing/pacing/defibrillation. These electrodes have a surface area of from a few square millimeters to several tens of square millimeters.

As shown in FIG. 4*e*, capsule body 100 houses a circuit 110 containing the active elements, the power supply battery, the sensors, and the connections to the electrodes. Circuit 110 is housed in body 102 of the capsule 14 which is sealed by lid 104, for example, by welding to cylindrical body 102. The central part of lid 104 may optionally include a conductive surface 112 forming a ground electrode, isolated from the rest of body 102 by a peripheral ring 114 made of an insulating material.

Base 200 includes a plate 202 on which the bottom surface 106 of body 102 is supported. The underside of plate 202 bears the anchoring structure to anchor base 200 to the patient's cardiac wall, which in this embodiment is a helical screw 204 of 2 to 3 mm in diameter.

On the opposite side, that is to say the side facing capsule body 100, plate 202 is provided with a generally rectangular shape having a major axis and at each of its ends a projecting tab 206. In this embodiment, projecting tab 206 are elastically deformable. The plate 202 and projecting tabs 206 are advantageously made of medical grade Tecothane (registered trademark). Projecting tabs 206 extend upwardly in a substantially parallel direction and have in their opposing faces a slight concavity 208, matching and in part overlapping the shape of the combined peripheral surface, preferably slightly convex, of body 102, so as to ensure the retention of capsule body 100 by clipping body 102 between the two elastically deformable projecting tabs 206.

Advantageously, as shown in FIG. 4*c* which discloses the entire capsule body 100/base 200 in a pacing configuration, protrusions 108 of capsule body 100, which carry the respective electrodes 22 and 24, are fit with no clearance or a very slight clearance against flanges 210 of the central portion of plate 202, thereby rotationally locking capsule body 100 relatively to base 200 and preventing any change in the stimulation zones, that is to say zones of the heart wall located in contact with each of the two electrodes 22 and 24. It should be noted that, for contact with the heart to be effective, the thickness of projecting elements 108 must be greater than the thickness of the central part of plate 202.

In an alternative embodiment, the stimulation (and/or detection) electrodes in contact with the tissues to be stimulated are formed on base 200 and not on capsule body 100. In this case, body 102 of capsule body 100 is provided with electrodes coupled to contacts arranged on the inside of base 200, which contacts are in turn connected to electrodes on the outside of base 200, in contact with patient tissues. This embodiment makes possible in particular stimulation via the anchoring structure of the base fixed to the tissues, e.g. by anchoring screw 204.

According to another aspect of the invention, base 200 and/or capsule body 100 may be provided with radiopaque markers to facilitate future operations of extraction of capsule body 100 and then of setting up and fastening a new capsule body 100 on base 200, which base 200 is left implanted in situ.

FIGS. 5*a* and 5*b* illustrate a second embodiment of the autonomous active implantable device of the present invention, for an endocardial capsule with clip fastening the capsule body to the base. In this embodiment, capsule body 100 is in the form of an elongated member with an elongated body terminated with two domed ends 118. The capsule body has a longitudinal dimension of the order of 10 mm, and a maximum diameter of a few millimeters. Note that in this configuration, capsule body 100 is disposed with its longitudinal axis oriented in a direction D1 substantially parallel to the cardiac wall, that is to say perpendicular to the axis D2 of the anchoring system 204 of base 200—unlike the previous embodiment illustrated in FIGS. 4*a*-4*e*, wherein the two axes are essentially aligned and combined.

Base 200 comprises two elastic tabs 214 defining on their inner sides, a concave surface 216, which is a complementary counterpart to outer surface 116 of capsule body 100. The length of tabs 214 is such that ends 220 thereof are beyond the diameter region of capsule body 100, so as to ensure retention in place thereof after capsule body 100 has been fitted into base 200, again with a snap-fit fastening connection.

Capsule body 100 is preferably provided on both sides of base 200 with two annular rings 120, arranged near ends 118 in the form of an ogive and carrying electrodes 22, 24 in the form of conductive surfaces over the entire periphery of rings 120. This configuration allows contact with heart tissue regardless of the method by which capsule body 100, which has symmetry of revolution about the axis D1, has been fitted onto base 200. It also provides a relatively large spacing between electrodes 22 and 24, in favor of more effective stimulation.

It should be understood that the small diameter (e.g., a few millimeters) of capsule body 100 allows for a very atraumatic introduction to the implantation site. The capsule body 100 is then turned a quarter turn at the time of fitting onto base 200, so as to orient it with the axis D1 of the capsule perpendicular to the axis D2 of the base and of the anchoring system screw.

In an alternative embodiment (not illustrated), the system has several, typically two, bases set side by side on the heart wall and onto which a single capsule body is fit. The device is thus attached to the wall at several, typically two, locations, which increases the contact surface and provides greater freedom as regards the choice of the stimulation sites, and a better mechanical resistance due to the absence any of preferred rotation or bending axis.

FIGS. 6*a* and 6*b* illustrate a third embodiment of the leadless capsule in accordance with the present invention, for a capsule with epicardial fixation by screwing the capsule body onto the base. In this configuration, projecting tabs 206 of base 200 are provided on their inner faces with a thread 224 fitting with a complementary thread 122 formed on the counterpart outer surface body 102. The setup of capsule body 100 on base 200 is then performed by screwing. Lid 104 of the capsule body is advantageously provided with recesses 124 for engaging a tool to effect rotation of the capsule body.

In FIG. 6*b*, an embodiment in which the autonomous active implantable medical implant can include a plurality of stacked capsule bodies such as 102, 102' is illustrated: body 102 is reversibly coupled to the base by a fastening system as described above, and encloses for example all the electronic circuits. On the other hand, body 102' is superimposed on and secured to body 102 using a second fastening system, and contains the power supply. In this way, body 102' can be replaced while leaving in place body 102 mounted on base 200 and base 200 anchored to the patient's tissue. A suitable electrical connection is provide to electrically couple the power supply to the electronic circuits when bodies 102 and 102' are fastened together in a stack.

FIGS. 7*a* to 7*c* illustrate a fourth embodiment of the autonomous active implantable medical device of the present invention, for an epicardial capsule with fixation to the base by a bayonet mounting system. In this configuration, projecting tabs 206 are rigid and each includes a curved guiding notch 226, 228 having a "J"-like channel dimensioned to cooperate with a coupling finger 126 formed on and projecting from a side wall of capsule body 100. The implementation is in the same manner as a conventional bayonet coupling for an electric lamp base and bulb or camera lens and body system, by a "pushed-turned" movement. The retention of for examples two fingers 126 in respective notches 226, 228 is provided by elastic material elements 230 formed on plate 202. These elastic elements 230 ensure that, once the movement of introduction of capsule body 100 into base 200 is completed, coupling fingers 126 are biased securely in the bottom 228 of the curved guiding notch 226.

In this embodiment, the stimulation electrodes 22, 24 are carried by projecting elements 128 formed on the lower surface of the capsule 100 body and intended to come into contact with heart tissue once the capsule body 100 is fitted on base 200.

One skilled in the art will appreciate that the present invention can be practiced by other than the embodiments disclosed herein, which are provided for purposes of illustration and explanation and not of limitation.

The invention claimed is:

1. An intracorporeal autonomous active medical device, comprising:

a sealed capsule body having an external shape and containing therein electronic circuitry, and a base comprising a plate having two opposing ends, an outer face and an inner face, an anchoring structure connected to said outer face to anchor said base to a wall of an organ of a patient, said inner face comprising a support for the capsule body and a fastening system to mechanically fasten in a reversible manner said base to said capsule body;

wherein the fastening system comprises at least two projecting tabs disposed in opposition at said two opposing ends of the plate, said projecting tabs being substantially parallel and having opposing faces, said opposing faces defining contact surfaces matching the shape of a corresponding surface of the capsule body for mechanical fastening thereto.

2. The device of claim 1, wherein the corresponding surface of the capsule body shape further comprises at least two convex contact surfaces, the projecting tabs are elastically deformable, and the protecting tabs contact surfaces further comprise opposing concavities matching the corresponding convex contact surfaces of the capsule body, for a reversible fastening by clipping of the capsule body on the base.

3. The device of claim 1, wherein the corresponding capsule body shape further comprises at least a first threaded surface, the projecting tabs are rigid tabs, and the opposing contact surfaces of the projecting tabs further comprise threaded surfaces corresponding to and threadably engageable with said first threaded surface for reversible fastening by screwing of the capsule body to the base.

4. The device of claim 1, wherein the corresponding capsule body shape further comprises at least two coupling fingers and the projecting tabs are rigid and comprise curved notches for engaging with said coupling fingers, for a bayonet mount reversible fastening of the capsule body on the base, the base further comprising a resilient material, said resilient material biasing the capsule body in the axial direction for locking the capsule body coupling fingers in the curved notches and the capsule body fastened to the base.

5. The device of claim 1, wherein the base further comprises at least one electrode on the outer face for contacting the wall of the patient's organ, the capsule body further comprises an electrode and the base further comprises an electrical contact on said inner face, said electrical contacts being connected to at least one electrode formed on the outer face of the base for contacting the wall of the patient's organ, and wherein said capsule body electrodes are connected to said base electrical contacts when said capsule body is fastened to said base.

6. The device of claim 1, wherein the anchoring structure has an axis that is normal to the wall of the patients' organ and the corresponding capsule body shape further comprises an elongated shape having a major axis oriented parallel to the axis of the anchoring structure; and wherein the capsule body further comprises at least one support projection carrying an electrode surface disposed to contact the tissues of the patient when the capsule body is fastened to the base.

7. The device of claim 6, wherein the base plate further comprises a flange and the capsule body support projection further comprises a side wall positioned to contact said flange of the plate and to lock against axial rotation of the capsule body relatively to the base.

8. The device of claim 6, wherein the capsule body comprises, on its face opposite to that facing the base, a lid having a conductive surface forming a ground electrode, for coming in contact with a patient's body fluid when the capsule body is fastened on the base.

9. The device of claim 6, wherein the capsule body comprises, on its face opposite to that facing towards the base, means for fastening an additional element separable from the capsule body without separation of the capsule body from the base, the body and the additional element thereby forming a stack.

10. The device of claim 9, wherein the additional element houses a power supply for the electronic circuits housed in the capsule body.

11. The device of claim 6 wherein the capsule body further comprises a first body and a second body, wherein the first body contains said corresponding shape fastening the first body to said projecting tabs of said base, and wherein said first and second bodies are mechanically fastened together in a reversible manner and can be uncoupled without uncoupling said first body from said base.

12. The device of claim 11 wherein the first body contains said electronic circuitry and the second body contains a power supply, wherein said power supply is electrically connected to energize said electronic circuitry when said first and second bodies are mechanically fastened together in a stack.

13. The device of claim 1, wherein the anchoring system further comprises an axis normal to the wall of the patient tissue and the corresponding capsule body shape further comprises an axis that is oriented perpendicularly to the axis of the anchoring structure, and wherein the capsule body comprises an elongated shape having at least one axial end region, and an annular ring positioned at said axial end, having an electrode surface for coming into contact with the tissues of the patient when the capsule body is fastened to the base.

14. The device of claim 1, wherein at least one of the capsule body and the base further comprises a radio-opaque marker.

* * * * *